(12) United States Patent
Bays

(10) Patent No.: US 6,269,820 B1
(45) Date of Patent: Aug. 7, 2001

(54) METHOD OF CONTROLLING POST-OPERATIVE LEAKAGE ASSOCIATED WITH TUMESCENT LIPOSUCTION

(75) Inventor: F. Barry Bays, Jacksonville, FL (US)

(73) Assignee: Xomed Surgical Products, Inc., Jacksonville, FL (US)

( * ) Notice: Subject to any disclaimer, the term of this patent is extended or adjusted under 35 U.S.C. 154(b) by 0 days.

(21) Appl. No.: 09/257,926

(22) Filed: Feb. 26, 1999

Related U.S. Application Data
(60) Provisional application No. 60/077,770, filed on Feb. 26, 1998.

(51) Int. Cl.[7] ............................. A61B 19/08; A61F 13/36
(52) U.S. Cl. ......................... 128/898; 604/542; 604/378; 604/385.03; 604/385.08
(58) Field of Search ................... 128/898; 604/28, 604/35, 358, 337, 365, 378, 902, 385.03, 385.08, 542

(56) References Cited

U.S. PATENT DOCUMENTS

| | | |
|---|---|---|
| D. 256,162 | 7/1980 | Haerr et al. . |
| 3,157,178 | 11/1964 | Bentov . |
| 3,648,692 | 3/1972 | Wheeler . |
| 3,797,491 | 3/1974 | Zaffaroni . |
| 3,814,095 | 6/1974 | Lubens . |
| 3,900,027 | 8/1975 | Keedwell . |
| 3,934,587 | 1/1976 | Gordon . |
| 3,996,934 | 12/1976 | Zaffaroni . |
| 4,034,759 | 7/1977 | Haerr . |
| 4,054,141 | 10/1977 | Schwaiger et al. . |
| 4,060,084 | 11/1977 | Chandrasekaran et al. . |
| 4,096,230 | 6/1978 | Haerr . |
| 4,098,728 | 7/1978 | Rosenblatt . |
| 4,122,857 | 10/1978 | Haerr . |
| 4,159,719 | 7/1979 | Haerr . |
| 4,286,592 | 9/1981 | Chandrasekaran . |
| 4,292,972 | 10/1981 | Pawelchak et al. . |
| 4,379,454 | 4/1983 | Campbell et al. . |
| 4,381,611 | 5/1983 | Wishman . |
| 4,430,447 | * 2/1984 | Popspich et al. ............... 521/63 |
| 4,467,806 | 8/1984 | Bhiwandiwala et al. . |
| 4,502,156 | 3/1985 | Wishman . |
| 4,540,414 | 9/1985 | Wishman . |
| 4,550,725 | 11/1985 | Wishman . |
| 4,568,343 | 2/1986 | Leeper et al. . |
| 4,573,995 | 3/1986 | Chen et al. . |
| 4,588,400 | 5/1986 | Ring et al. . |
| 4,615,699 | 10/1986 | Gale et al. . |
| 4,660,553 | 4/1987 | Naylor et al. . |
| 4,664,662 | 5/1987 | Webster . |
| 4,733,659 | 3/1988 | Edenbaum et al. . |
| 4,753,231 | 6/1988 | Lang et al. . |
| 4,764,379 | 8/1988 | Sanders et al. . |
| 4,863,738 | 9/1989 | Taskovich . |
| 4,925,453 | 5/1990 | Kannankeril . |

(List continued on next page.)

OTHER PUBLICATIONS

Article entitled "The New Art of Body Liposuction Contouring", William P. Coleman, III, M.D. et al., pp. 1–8 & 53–57.

*Primary Examiner*—Corrine McDermott
*Assistant Examiner*—Choon Koh

(57) ABSTRACT

A method of controlling fluid leakage from an incision following tumescent liposuction and other surgical procedures where large amounts of fluid are introduced into the body includes placing a highly absorbent pad composed of a softened polyvinyl acetate sponge over the incision and holding the pad in place using a flexible backing with adhesive on one side. The softened polyvinyl acetate sponge material can be placed over the incision in either an unexpanded dry state or an expanded dry state. In one embodiment, a liquid impermeable layer is formed on one side of the pad and positioned on the adhesive side of the backing to prevent the absorbed fluids from infiltrating the backing.

16 Claims, 3 Drawing Sheets

U.S. PATENT DOCUMENTS

| | | |
|---|---|---|
| 4,961,735 | 10/1990 | Siciliano . |
| 4,967,758 | 11/1990 | Masciarotte . |
| 4,997,425 | 3/1991 | Shioya et al. . |
| 5,006,342 | 4/1991 | Cleary et al. . |
| 5,009,562 | 4/1991 | Morgan et al. . |
| 5,019,064 | 5/1991 | Eilender . |
| 5,066,494 | 11/1991 | Becher . |
| 5,071,648 | 12/1991 | Rosenblatt . |
| 5,078,709 | 1/1992 | Siciliano . |
| 5,098,775 | 3/1992 | Harada et al. . |
| 5,336,163 | 8/1994 | DeMane et al. . |
| 5,370,689 | 12/1994 | Causse . |
| 5,387,206 | 2/1995 | Valentine et al. . |
| 5,447,493 * | 9/1995 | Blugerman et al. .................. 604/35 |
| 5,447,505 | 9/1995 | Valentine et al. . |
| 5,453,078 | 9/1995 | Valentine et al. . |
| 5,460,621 | 10/1995 | Gertzman et al. . |
| 5,466,231 | 11/1995 | Cercone et al. . |
| 5,469,864 | 11/1995 | Rosenblatt . |
| 5,505,958 | 4/1996 | Bello et al. . |
| 5,524,642 | 6/1996 | Rosenblatt . |
| 5,556,391 | 9/1996 | Cercone et al. . |
| 5,744,150 | 4/1998 | Cercone . |
| 5,817,050 * | 10/1998 | Klein ..................................... 604/35 |
| 5,928,665 * | 7/1999 | Cercone ............................... 424/445 |
| 5,950,238 * | 9/1999 | Klein ........................................ 2/69 |

* cited by examiner

METHOD OF CONTROLLING POST-OPERATIVE LEAKAGE ASSOCIATED WITH TUMESCENT LIPOSUCTION

CROSS-REFERENCE TO RELATED APPLICATIONS

This application claims priority from U.S. Provisional Patent Application Ser. No. 60/077,770, filed Feb. 26, 1998, the disclosure of which is incorporated herein by reference.

BACKGROUND OF THE INVENTION

1. Field of the Invention

The present invention relates generally to methods of controlling fluid leakage from wounds and, more particularly, to a method of controlling fluid leakage from a tunnel formed in fatty tissue as part of a tumescent liposuction surgical procedure during which large amounts of a tumescent solution are introduced into the fatty tissue.

2. Description of the Background Art

Liposuction is a surgical technique which is widely used to permanently remove excess fat in areas of the body which are resistant to diet and exercise. Early forms of fat removal surgery involved extracting blocks of fat from the body through large incisions, often resulting in long unsightly scars. Liposuction, on the other hand, utilizes an elongate tube with an opening at each end, called a cannula, which is inserted into the body via small incisions and attached to a suction device to remove large amounts of fat with less scarring. While early forms of liposuction were an improvement over large excisions of fat, the instruments were still large, general anesthesia was necessary, bleeding and bruising were commonplace, and recovery tended to be long and difficult.

A more recent approach to liposuction, known as tumescent liposuction or liposculpture, involves infusing large volumes (i.e., many liters) of a very dilute solution of local anesthesia and adrenalin into the areas to be suctioned. This tumescent solution provides the local anesthesia during the procedure allowing the patient to remain awake and comfortable and avoiding the risks of general anesthesia. Large amounts of the dilute adrenalin in the tumescent solution constricts the blood vessels thereby reducing bleeding and bruising to a minimum and allowing the surgeon to spend more time shaping the areas for optimal results. While tumescent liposculpture is an improvement over the older forms of liposuction, leakage of the tumescent solution from the tiny incisions may occur for up to eighteen hours following the procedure. To control fluid leakage, cosmetic surgeons typically place a gauze pad over the portal and secure it with standard surgical tape. As the gauze becomes saturated, however, some of the fluid can seep through the tape thereby adding to the discomfort of the patient by soaking clothing and necessitating frequent substitution of bandages.

SUMMARY OF THE INVENTION

Accordingly, it is an object of the present invention to overcome the above mentioned disadvantages of the prior art by improving methods of controlling fluid leakage from an incision following tumescent liposuction and other types of surgical procedures where large amounts of fluid are introduced into the body.

Another object of the present invention is to improve patient comfort following tumescent liposuction and other types of surgical procedures by increasing the amount of fluid absorbed by a bandage placed over an incision and retaining the absorbed fluid within the bandage.

A first aspect of the present invention is generally characterized in a method of controlling postoperative fluid leakage following a tumescent liposuction surgical procedure during which large volumes of a tumescent solution are infused into fat tissue, including the steps of providing a bandage having an aborbent pad formed of expanded polyvinyl acetate sponge material with a softer outer texture than dry, rigid polyvinyl acetal sponge material, placing the expanded absorbent pad over the opening of a tunnel formed in the fat tissue with a cannula as part of the tumescent liposuction surgical procedure, holding the expanded absorbent pad against the tunnel opening using a flexible backing with adhesive on one side so that tumescent solution leaking from the tunnel is absorbed by the pad, and containing the absorbed tumescent solution within the absorbent pad by interposing a liquid impermeable layer between the absorbent pad and the backing.

Another aspect of the present invention is generally characterized in a method of controlling postoperative fluid leakage following a tumescent liposuction surgical procedure during which large volumes of a tumescent solution are infused into fat tissue, including the steps of placing an expandable absorbent pad in an unexpanded, dry state over the opening of a tunnel formed in the fat tissue with a cannula as part of the tumescent liposuction surgical procedure, holding the expandable absorbent pad against the tunnel opening using a flexible backing with adhesive on one side so that tumescent solution leaking from the tunnel is absorbed by the pad as the pad expands from the dry state to an enlarged wet state, and containing the absorbed tumescent solution within the enlarged absorbent pad by interposing a liquid impermeable layer between the absorbent pad and the backing.

Still another aspect of the present invention is generally characterized in a method of performing tumescent liposuction including the steps of introducing a tumescent solution into fatty tissue in the body, removing fatty tissue by forming one or more tunnels in the fatty tissue via an opening, placing a bandage containing a softened polyvinyl acetal sponge over the opening, and absorbing tumescent solution leaking from the opening in the sponge. The softened polyvinyl acetate sponge material can be placed over the incision in either an unexpanded dry state or an expanded dry state.

Yet another aspect of the present invention is generally characterized in a bandage for controlling post-operative leakage of fluid following tumescent liposuction including a flexible backing with adhesive on one side, and an absorbent pad formed of a softened polyvinyl acetal sponge material with a liquid impermeable surface positioned on the adhesive side of the backing. The softened polyvinyl acetal sponge material has a thickness in a dry state to absorb and retain between 15 and 200 cc of the tumescent fluid so that the bandage can remain in place for about 8 to 12 hours before having to be replaced. The polyvinyl acetal sponge material can be provided in an expanded dry state such that there is little or no enlargement of the sponge material during absorbtion or the sponge material can be provided in an unexpanded dry state so as to expand in size as the fluid is absorbed. The shape and size of the polyvinyl acetal sponge material can be configured to cover one or more incisions. The surface area of the polyvinyl acetal sponge material is preferably less than that of the backing so that an adhesive margin or border remains around the perimeter of the sponge material to permit the bandage to be adhesively secured to the patient at the operative site.

Some of the advantages of the present invention over the prior art are that the bandage does not need to be changed as frequently, that liquid and moisture vapor permeable materials can be used as a backing for the bandage without compromising the fluid controlling properties of the bandage, that the bandage can be provided in various shapes and sizes for use on different parts of the body, and that the amount of fluid absorbed by the bandage can be controlled by altering the density, thickness and/or surface area of the sponge body.

Other objects and advantages of the present invention will become apparent from the following description of the preferred embodiments taken in conjunction with the accompanying drawings, wherein like parts in each of the several figures are identified by the same reference numerals.

DESCRIPTION OF THE PREFERRED EMBODIMENTS

While the present invention is described hereinafter as a method of controlling post-operative fluid leakage associated with tumescent liposuction, it will be appreciated that the method can be used to control fluid leakage after any type of surgical procedure involving introduction of fluids into the body via small incisions or portals, such as arthroscopy.

Figure 2:
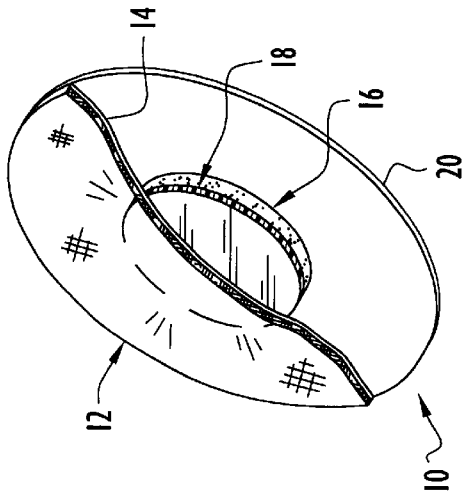
FIG. 2 is a perspective cut-away view of the absorbent bandage shown in FIG. 1.
Figure 1:
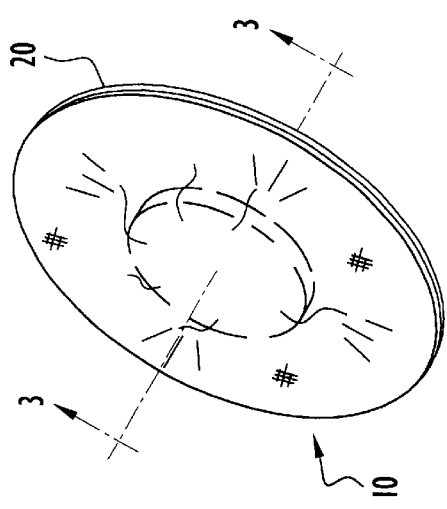
FIG. 1 is a perspective view of an absorbent bandage for use in controlling post-operative leakage of a tumescent solution following a tumescent liposuction surgical procedure.
Figure 3:
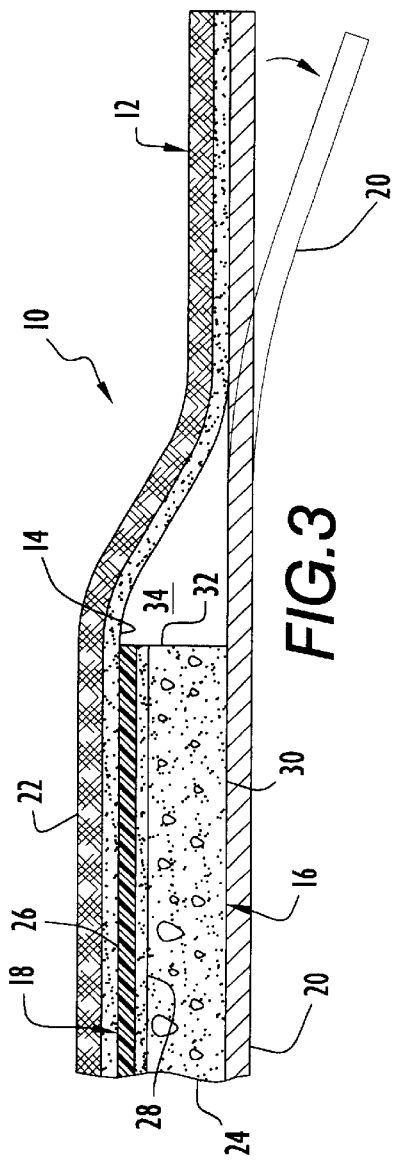
FIG. 3 is a fragmentary sectional side view of the absorbent bandage taken through line 3—3 in FIG. 1.

A bandage 10 for use in accordance with the method of the present invention, as illustrated in FIGS. 1–3, includes a flexible backing 12 with an adhesive 14 on one side and an absorbent pad 16 with a liquid impermeable layer or film 18 positioned on the adhesive side of the backing, the cross-sectional area of the pad being less than that of the backing so that an adhesive margin or border remains around the perimeter of the pad to permit the bandage to be adhesively secured to the patient at the puncture site or incision. A peelable film or layer 20 covers the adhesive margin and the bottom surface or face of the absorbent pad until the bandage is ready to be used.

Backing 12 includes a thin, circular sheet of a flexible and, preferably, porous material 22 having a pressure sensitive adhesive 14 on one side. The backing is flexible or pliant to conform to the contours of a patient's body and is preferably porous and breathable to permit gaseous exchange at the wound site. Various woven and non-woven fabrics can be used as a backing in accordance with the present invention including, but not limited to, paper, nylon, polyester and rayon fabrics. Any medical grade adhesive suitable for temporarily and removably securing bandages to the skin of a patient can be used, and it will be appreciated that the adhesive can be applied over all or part of the backing material on one side. A suitable backing for the present invention is the bandage sold by 3M Corporation as product no. 1776 which is formed of a white spun laced polyester non-woven tape with a hypoallergenic pressure sensitive acrylic adhesive applied continuously over one side of the tape.

In a first embodiment, shown in FIGS. 1–5, pad 16 includes an absorbent body 24 of cylindrical or disc-like configuration with a liquid impermeable layer or film 18 on one side. The absorbent body 24 is preferably made of an open-celled sponge material of the type which normally absorbs fluids by expanding substantially from its size in a dry state, such as a polyvinyl acetal sponge material as described in U.S. Pat. No. 4,098,728, the disclosure of which is incorporated herein by reference. Commercially available polyvinyl acetal sponge products are sold by Merocel Corporation under the grade designations CF50, CF100 and CF150. These grade designations have respective average pore diameters of 0.95 mm, 0.45 mm and 0.35 mm and an overall range of pore diameters of between about 0.004 mm and about 1.2 mm. The polyvinyl acetal sponge material is a homogeneous white, open-celled sponge with visible pores, instantaneous fluid wicking, absorptive capacity of up to 25 times its weight in fluids, a retained fluid capacity of 16 times its own weight in fluids as measured by ASTM D-1117-80, and a pore size range (diameter) of between about 0.02 and about 1.2 mm as determined by Scanning Electron Microscopy at 10× magnification. The commercially available polyvinyl acetal sponge material is normally rigid in a dry state but can be processed to have greater flexibility and a softer outer texture than dry, rigid polyvinyl acetal sponge material, for example using the process described in U.S. Pat. No. 5,744,150, the disclosure of which is incorporated herein by reference. Furthermore, while the commercially available polyvinyl acetal sponge material normally expands substantially in size as it absorbs fluids, the material can be provided in an expanded dry state so that there is little or no expansion of the pad as fluids are absorbed. The preferred material for the pad is Merocel CF50 polyvinyl acetal sponge material which has been softened and expanded to a thickness of between about 15 and about 25 mm in a dry state to absorb large amounts of fluid (e.g., between about 15 and about 200 cc).

The liquid impermeable layer 18 is preferably formed by laminating a liquid impermeable polymeric film 26 to the absorbent body 24 with an adhesive 28. There are many polymeric films available for laminating to the absorbent body as a liquid impermeable layer 18. For example, polyolefins such as polyethylene, halogenated polyolefins such as polytetrafluoroethylene (PTFE), polyesters such as polyethylene terephthalate (PET) and polyurethanes can be used. The polymeric film thickness is specified thick enough to facilitate ease of handling and adequate strength (to prevent tearing) while being thin enough, generally in the range of about 0.0005 to about 0.0030 inches in thickness, to not substantially affect the bulk properties of the absorbent body in the composite laminated product. In the case of a polyethylene film or liner, a preferred thickness is about 0.001 inches. Lamination with a polymeric film layer such as polyethylene can be achieved using any suitable medical grade adhesives such as, for example, unsupported acrylic-based adhesives. Alternatively, known ultrasonic sealing or melt processing techniques can be used to laminate the absorbent body with a polymeric film. It is also possible to form a liquid impermeable layer or film 18 by fusing one surface of the absorbent body, for example using a press equipped with a hot plate.

One method of constructing the absorbent pad 16 includes forming the sponge body 24, slicing or otherwise cutting the sponge body to the desired thickness, placing a layer of adhesive 28 on the body surface to be covered and then placing the polymeric film 26 over the adhesive. The composite is then cured, and diecutting of the composite is performed to produce desired shapes and sizes.

The bandage 10 of the present invention can be assembled by positioning the laminated or liquid impermeable side of the absorbent pad 16 against the adhesive side of the backing 12 such that the pad is secured to the backing with an adhesive margin or border remaining around the perimeter of the pad to permit the bandage to be adhesively secured to the patient at the puncture site or incision. The width of the adhesive margin or border will depend in part on the shape of the bandage and the adhesive used but will generally range from about 0.5 cm to about 3.0 cm. While it is convenient to use the same adhesive to secure absorbent pad 16 to backing 12 and marginal or peripheral portions of the backing to the body, it will be appreciated that different types of adhesive can be used (e.g., by coating an annular portion of the backing with a skin-contacting adhesive and a central portion of the backing with an absorbent pad adhesive). The peelable film 20 is placed over the adhesive margin and the non-laminated (i.e., liquid permeable) surface or face 30 of the sponge body to ease application and prevent contamination. In the assembled condition, backing 12 extends downwardly, looking at FIG. 3, from the laminated or liquid impermeable side of pad 16 to peelable film 20 at an angle to prevent non-laminated or liquid permeable portions or side walls 32 of sponge body 24 from contacting backing 12 by defining an annular space 34 between the backing and the non-laminated portions of the sponge body. Under certain circumstances, however, the backing can be configured to lay against non-laminated portions of the pad without any gaps or spaces. Bandage 10 is preferably stored in a sterile package or container for removal immediately prior to use.

A typical tumescent liposuction surgical procedure involves infusing large volumes of a very dilute tumescent solution into fat tissue using an infiltration cannula attached to a pump and removing the fat tissue using a cannula attached to a suction device. The cannula is introduced into the fat tissue via an opening or incision in the skin, and is typically moved around beneath the skin to form a plurality of tunnels in the fat tissue. The tumescent solution, which is usually composed of local anesthesia and adrenalin, provides the local anesthesia during the procedure allowing the patient to remain awake and comfortable and avoiding the risks of general anesthesia. Large amounts of the dilute adrenalin in the tumescent solution constricts the blood vessels thereby reducing bleeding and bruising to a minimum and allowing the surgeon to spend more time shaping the areas for optimal results. However, once the cannula is removed, the tumescent fluid can leak from the incision for as much as eighteen hours following the procedure.

Figure 4:
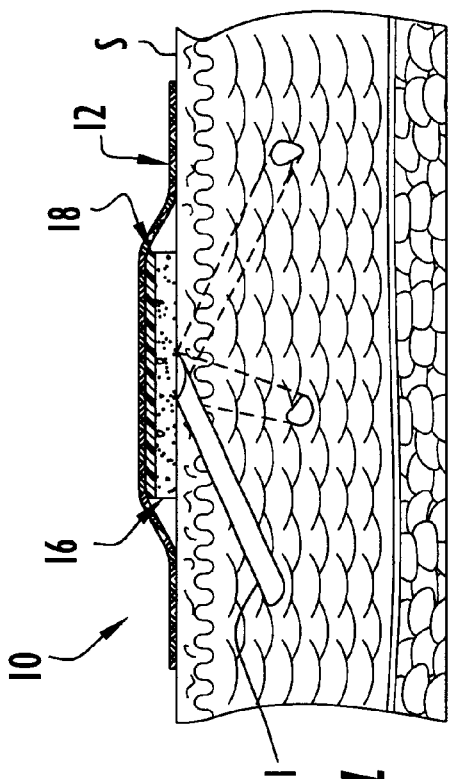
FIGS. 4 and 5 are side views, in section, illustrating use of the absorbent bandage of FIG. 1 to control post-operative leakage of tumescent solution following a tumescent liposuction surgical procedure.
Figure 5:
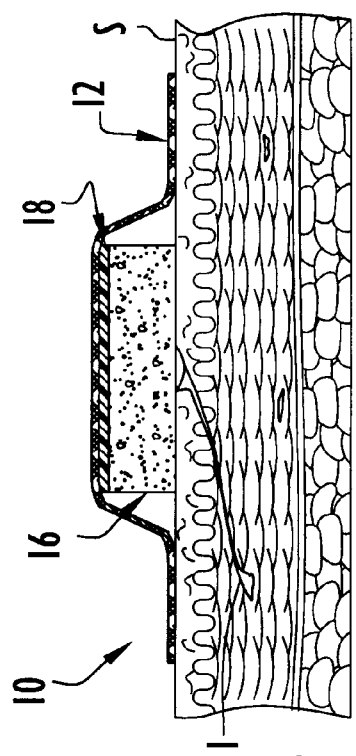

Post-operative leakage of fluid following tumescent liposuction can be controlled using bandage 10. If provided in a sterile package, bandage 10 is removed from the package and placed over one or more of the incisions formed in the skin as portals for the suction cannula. Once removed from the sterile package, film 20 is peeled away from backing 12 to expose the non-laminated surface 30 of sponge body 24 as shown by broken lines in FIG. 3. The non-laminated surface 30 of the sponge body is then located over the incision or wound I, and the adhesive margin of the backing 12 is pressed against the skin S to secure the bandage to the body of the patient as shown in FIG. 4. Since the backing 12 is flexible and pliant, the bandage will tend to conform to the shape of the body and move with the skin without bunching in order to hold the sponge body against the incision during normal activities. The absorbent body 24 shown in FIG. 4 is initially in an unexpanded dry state when applied over the incision but will immediately begin absorbing fluid and expand as shown in FIG. 5. In the case of a polyvinyl acetal sponge body, the pad 16 can absorb as much as about 25 times its own weight in fluid, the total amount of fluid absorbed being dependent upon the surface area, thickness and density of the sponge body. For example, if sponge body 24 of the pad is formed of Merocel CF50 polyvinyl acetal sponge material formed into about a 4 cm diameter disk having a thickness when dry of about 5 mm, the pad will absorb about 15 cc of fluid and expand to about 15 mm in thickness. Expansion of pad 16 can cause backing 12 to stretch and/or marginal or peripheral portions of the backing to draw inwardly, toward to the pad, depending on the backing material chosen. In the latter case, movement of the marginal portions of the bandage can have the effect of drawing skin inwardly in the direction of the incision. If desired, the portion of the backing suspended between the pad and the peelable film (i.e., defining the gap or space 34) can be left somewhat slack or loose to accommodate expansion of the pad without stretching the backing material or drawing peripheral portions of the backing inwardly. The polyvinyl sponge material has a thickness in a dry state to absorb and retain between 15 and 200 cc of the tumescent fluid so that the bandage can remain in place for about 8 to 12 hours before having to be replaced. Since the liquid impermeable side of the pad is adhered to the backing, the pad is easily removed with the backing when it is time to replace the bandage.

Alternatively, post-operative leakage of the tumescent fluid can be controlled using a bandage with an absorbent pad formed of a polyvinyl acetal sponge provided in an expanded dry state and having a softer outer texture than dry, rigid polyvinyl acetal sponge material so that there is little or no enlargement of the absorbent pad in use. While an expanded pad formed of polyvinyl acetal sponge material is capable of absorbing about the same amount of fluid as an unexpanded pad formed of the same material, the backing for an expanded pad does not need to be designed to accommodate expansion. A bandage with a polyvinyl acetal sponge provided in an expanded dry state will resemble the bandage with the enlarged wet sponge shown in FIG. 5.

As mentioned above, a large volume of tumescent solution can leak from the incision for as much as eighteen hours following the procedure. Conventional bandages are quickly saturated and must typically be replaced every hour. The bandage according to the present invention, however, is capable of absorbing large amounts of fluid (e.g., as much as about 15 to 200 cc) and can therefore remain in place for about 8 to 12 hours before being replaced. Moreover, by positioning the laminated or liquid impermeable side of the pad 16 against the backing, a liquid impermeable barrier is established which prevents anesthetic fluid and other types of exudate from infiltrating the backing material. Since the leakage of anesthetic fluid following tumescent liposuction is often cited as the worst part of the procedure, a bandage which can capture most, if not all, of the fluid while maintaining a substantially dry outer surface or backing can significantly reduce postoperative discomfort for the patient.

Figure 6:
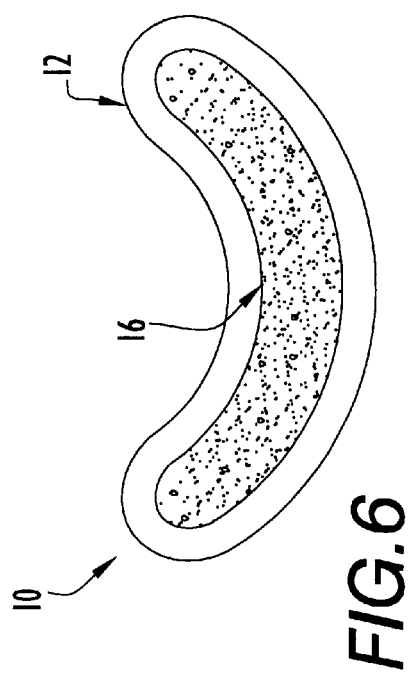

The absorbent bandage of the present invention can have various shapes for use in different areas of the body. For example, a modification of a bandage according to the present invention is shown in FIG. 6 wherein the modified bandage 10 is similar to the bandage described above but with an arcuate or banana-shaped backing 12 and a similarly shaped absorbent pad 16. Pad 16 of the modified bandage is of smaller cross-sectional area than backing 12 so that, when the laminated or liquid impermeable side of the pad is placed on the adhesive side of the backing, an adhesive margin or border remains around the pad having a width about the same as that of the adhesive margin or border described above.

Figure 7:
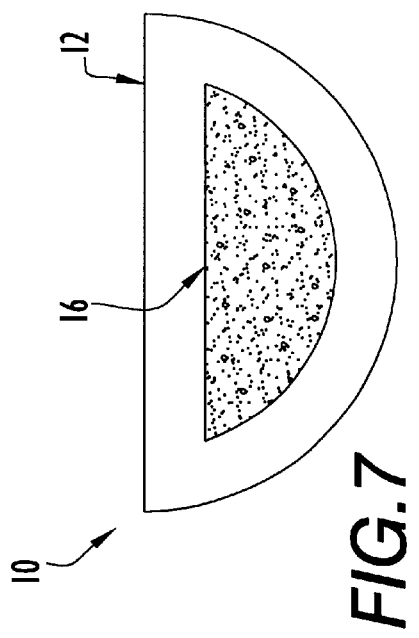
FIGS. 6, 7 and 8 are bottom plan views illustrating modifications of an absorbent bandage according to the present invention.

Another modification of an absorbent bandage for use according to the present invention, shown in FIG. 7 at 10, is similar to the bandages described above but with a semi-circular backing 12 and pad 16, the pad being of smaller cross-sectional area than the backing so that when it is positioned on the adhesive side of the backing an adhesive margin or border remains having a width about the same as that of the adhesive margins and borders described above.

Figure 8:
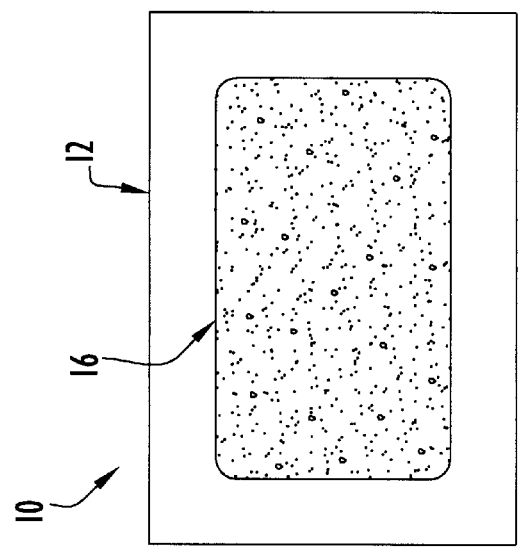

Yet another modification of an absorbent bandage for use according to the present invention, shown in FIG. 8 at 10, is similar to the bandages described above but with a generally rectangular backing 12 and pad 16, the pad being of smaller cross-sectional area than the backing so that when it is positioned on the adhesive side of the backing an adhesive margin or border remains having a width about the same as that of the adhesive margins and borders described above.

Various pad configurations which have been found useful for controlling postoperative leakage following tumescent liposuction are square pads about 11 inches on a side for covering the abdomen, rectangular pads about 5 inch by about 7 inch for general use, and banana shaped pads about 1.5 inches wide and about 6 inches long for covering a crevice area. The relatively large size of the pads and enormous fluid capacity permit the bandages to be placed over more than one incision if desired.

The absorbent bandage according to the present invention can be provided in an assembled condition as shown or in kit form with separate pad and backing components being assembled for use by surgical personnel or the patient. The backing can be of integral one-piece construction as shown or formed of multiple pieces or strips. If desired, the backing material can be stored within a dispenser for easy access in the doctor's office or surgical suite.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of controlling postoperative fluid leakage from a patient's body following a tumescent liposuction surgical procedure during which large volumes of a tumescent solution are infused into fat tissue, said method comprising the steps of providing a bandage having an absorbent pad formed of expanded polyvinyl acetal sponge material with a softer outer texture than dry, rigid polyvinyl acetal sponge material;

placing the expanded absorbent pad over the opening of a tunnel formed in the fat tissue with a cannula as part of the tumescent liposuction surgical procedure;

holding the expanded absorbent pad against the tunnel opening using a flexible backing with adhesive on one side so that at least a portion of the flexible backing is affixed to the patient's body via the adhesive and tumescent solution from the tunnel is absorbed by the expanded absorbent pad; and containing the absorbed tumescent solution within the expanded absorbent pad by interposing a liquid impermeable layer between the expanded absorbent pad and the backing.

2. A method as recited in claim 1 wherein the expanded absorbent pad has an absorptive fluid capacity of between about 15 and about 200 cubic centimeters.

3. A method as recited in claim 2 wherein the expanded absorbent pad has a thickness between about 15 mm and about 25 mm in the dry state.

4. A method as recited in claim 3 wherein a plurality of tunnels extend into the fat tissue from a respective plurality of tunnel openings and the expanded absorbent pad is positioned over more than one of the tunnel openings.

5. A method as recited in claim 1 wherein the liquid impermeable layer is formed as an integral part of the pad and said holding step includes placing the adhesive side of the backing against the liquid impermeable layer so that the pad is adhered to the backing for removal therewith.

6. A method of controlling postoperative fluid leakage from a patient's body following a tumescent liposuction surgical procedure during which large volumes of a tumescent solution are infused into fat tissue, said method comprising the steps of placing an expandable absorbent pad in an unexpanded, dry state over the opening of a tunnel formed in the fat tissue with a cannula as part of the tumescent liposuction surgical procedure;

holding the expandable absorbent pad against the tunnel opening using a flexible backing with adhesive on one side so that at least a portion of the flexible backing is affixed to the patient's body via the adhesive and tumescent solution leaking from the tunnel is absorbed by the pad as the pad expands from a dry state to an enlarged wet state; and containing the absorbed tumescent solution within the enlarged absorbent pad by interposing a liquid impermeable layer between the absorbent pad and the backing.

7. A method as recited in claim 6 wherein the absorbent pad has an absorptive fluid capacity of between about 15 and about 200 cubic centimeters.

8. A method as recited in claim 7 wherein the absorbent pad is made of an open-celled sponge material.

9. A method as recited in claim 8 wherein the open-celled sponge material is a polyvinyl acetal sponge material.

10. A method as recited in claim 9 wherein the polyvinyl acetal sponge material is flexible and has a softer outer texture than dry, rigid polyvinyl acetal sponge material.

11. A method as recited in claim 9 wherein the polyvinyl acetal sponge material is between about 15 mm and about 25 mm thick in the enlarged, wet state.

12. A method as recited in claim 6 wherein a plurality of tunnels extend into the fat tissue from a respective plurality of tunnel openings and the expandable absorbent pad is positioned over more than one of the tunnel openings.

13. A method as recited in claim 6 wherein the liquid impermeable layer is formed as an integral part of the pad and said holding step includes placing the adhesive side of the backing against the liquid impermeable layer so that the pad is adhered to the backing for removal therewith.

14. A method of performing tumescent liposuction comprising the steps of introducing a tumescent solution into fatty tissue in a patient's body;

removing fatty tissue by forming one or more tunnels in the fatty tissue via an opening;

placing a bandage having an adhesive and containing a softened polyvinyl acetal sponge over the opening so that at least a portion of the bandage is affixed to the patient's body via the adhesive; and absorbing tumescent solution leaking from the opening in the sponge.

15. A method as recited in claim 14 wherein the polyvinyl acetal sponge is placed over the opening in an unexpanded dry state and absorbs tumescent solution by expanding from the dry state to an enlarged wet state.

16. A method as recited in claim 14 wherein the polyvinyl acetal sponge is placed over the opening in an expanded dry state and absorbs tumescent solution without expanding significantly.

* * * * *